US00PP19812P3

(12) United States Plant Patent
Jensen

(10) Patent No.: US PP19,812 P3
(45) Date of Patent: Mar. 10, 2009

(54) ***CAMPANULA* PLANT NAMED 'PKMFOR168'**

(50) Latin Name: *Campanula formanekiana*
Varietal Denomination: PKMFOR168

(75) Inventor: Gert Kim Jensen, Norge (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 11/907,443

(22) Filed: Oct. 12, 2007

(65) Prior Publication Data

US 2008/0307552 P1 Dec. 11, 2008

(51) Int. Cl.
*A01H 5/00* (2006.01)

(52) U.S. Cl. ..... Plt./414

(58) Field of Classification Search ..... Plt./414, Plt./263

See application file for complete search history.

*Primary Examiner*—Annette H Para
*Assistant Examiner*—S. B. McCormick Ewoldt
(74) *Attorney, Agent, or Firm*—Foley & Lardner LLP

(57) ABSTRACT

A new and distinct cultivar of *Campanula* plant named 'PKMFOR168', characterized by having upright, compact plant habit; dense and bushy plant form, mainly due to short, upright and stiff stems; vigorous growth habit, but with no need for chemical growth retardation; higher number of flowers per plant; more cuttings on each stock plant; reduced need for cold treatment after flower induction; shorter period for forcing the flowers after the cold treatment; and deep violet-blue colored flowers.

5 Drawing Sheets

Latin name of genus and species of the plant claimed: *Campanula formanekiana.*
Variety denomination: 'PKMFOR168'.

BACKGROUND OF THE INVENTION

The present invention relates to a new and distinct cultivar of *Campanula* plant, botanically known as *Campanula formanekiana,* commonly known as Bellflower, and hereinafter referred to by the name 'PKMFOR168'.

The new *Campanula* 'PKMFOR168', is a product of a planned breeding program conducted by the inventor, Gert K. Jensen, in Søhus, Denmark. The objective of the breeding program is to develop a new *Campanula* cultivar with upright, compact plant form and deep violet flowers.

The new *Campanula* cultivar originated from a cross made in a controlled breeding program by the inventor in 2002 in Søhus, Denmark. The female or seed parent is an unpatented cultivar from the proprietary breeding line of *Campanula formanekiana* designated 11.02.2258. The male or pollen parent is an unpatented cultivar from the proprietary breeding line of *Campanula formanekiana* designated 11.02.2253. The new *Campanula* 'PKMFOR168' was discovered and selected by the inventor as a single flowering plant within the progeny of the stated cross in November of 2002 in a controlled environment in Søhus, Denmark. The inventor selected 'PKMFOR168' on the basis of its high number of cuttings per stock plant, short vernalization period, short forcing time after vernalization and deep violet-blue flowers.

Asexual reproduction of the new *Campanula* cultivar by terminal cuttings was first performed in November of 2003 in Søhus, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMFOR168'. These characteristics in combination distinguish 'PKMFOR168' as a new and distinct cultivar:

1. Upright, compact plant habit;
2. Dense and bushy plant form, mainly due to short, upright and stiff stems;
3. Vigorous growth habit, with no need for chemical growth retardation;
4. Higher number of flowers per plant;
5. More cuttings on each stock plant;
6. Reduced need for cold treatment after flower induction;
7. Shorter period for forcing the flowers after the cold treatment; and
8. Deep violet-blue colored flowers.

Plants of the instant cultivar 'PKMFOR168' differ primarily from plants of the unpatented, proprietary parental cultivars selected from the internal breeding lines of *Campanula formanekiana* designated by internal nos. 11.02.2258 (female or seed parent) and 11.02.2253 (male or pollen parent) by the following characteristics:

1. Plants of 'PKMFOR168' produce deeper blue-colored flowers than plants of the unpatented, proprietary parental cultivars selected from the internal breeding lines of *Campanula formanekiana* designated by internal nos. 11.02.2258 (female or seed parent) and 11.02.2253 (male or pollen parent); and
2. Plants of 'PKMFOR168' produce a higher yield of cuttings than plants of the unpatented, proprietary parental cultivars selected from the internal breeding lines of *Campanula formanekiana* designated by internal nos. 11.02.2258 (female or seed parent) and 11.02.2253 (male or pollen parent).

Side-by-side comparisons were conducted by the inventor in Stige, Denmark, among plants of the instant cultivar 'PKMFOR168' and plants of the most similar commercial cultivar, *Campanula formanekiana*. 'PKMF02' (unpatented, described in U.S. Plant patent application Ser. No. 11/713,745). Plants of the new *Campanula formanekiana* 'PKMFOR168' differ from plants of *Campanula formanekiana* 'PKMF02' in the following characteristics:

1. Plants of the 'PKMFOR168' produce deeper violet-blue flowers than plants of 'PKMF02';
2. Plants of 'PKMFOR168' have longer internodes and petioles than plants of 'PKMF02';
3. Plants of 'PKMFOR168' have longer flower peduncles than plants of 'PKMF02'; and
4. Plants of 'PKMFOR168' are taller in height than plants of 'PKMF02'.

BRIEF DESCRIPTION OF THE PHOTOGRAPHS

The accompanying colored photographs illustrate the overall appearance of the new *Campanula* 'PKMFOR168', showing the colors as true as it is reasonably possible to obtain in colored reproductions of this type. Colors in the photographs may differ slightly from the color values cited in the detailed botanical description, which more accurately describe the actual colors of 'PKMFOR168'.

DETAILED BOTANICAL DESCRIPTION

Figure 1:
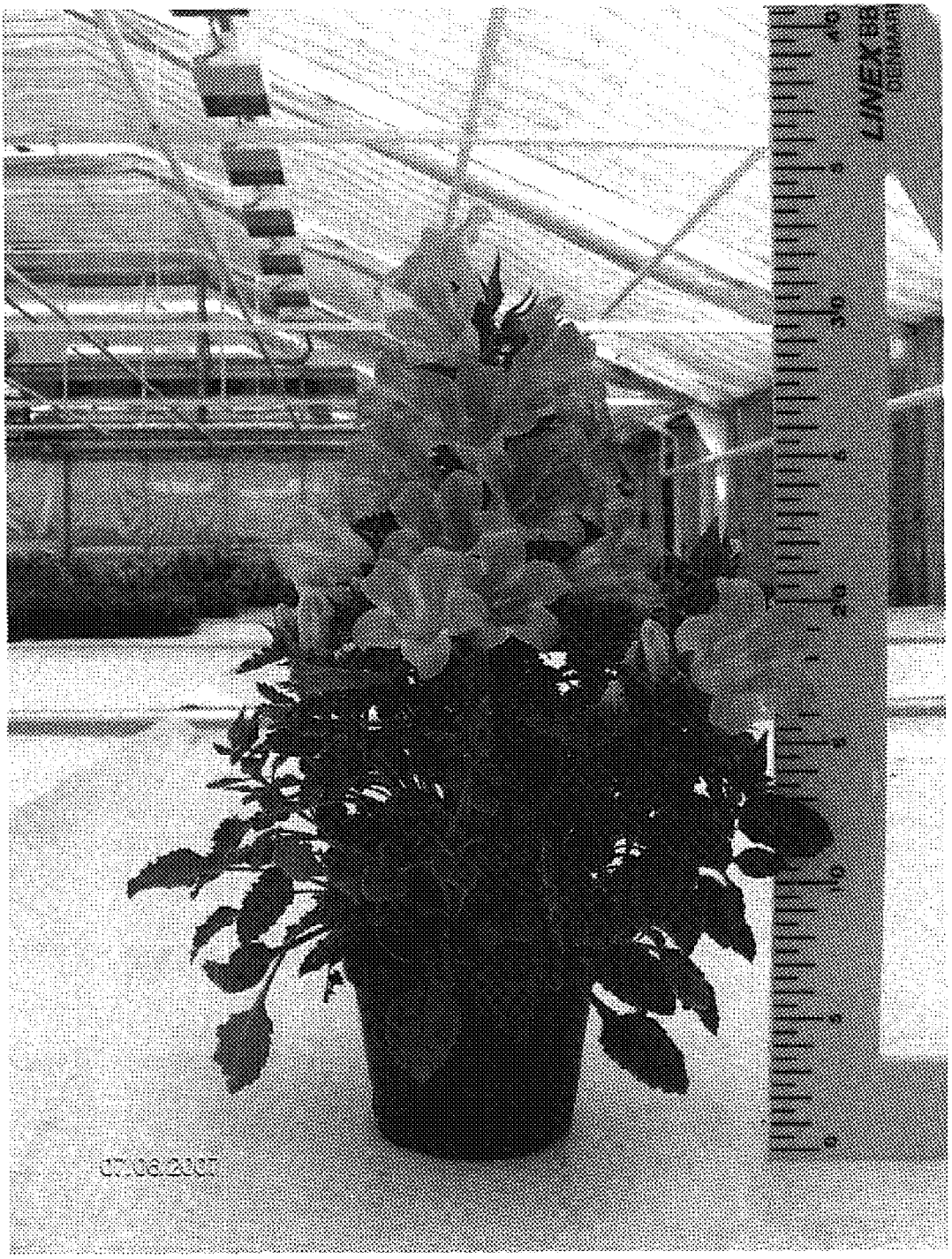
FIG. 1 shows a side perspective view of a typical flowering plant of 'PKMFOR168', as grown in a 10.5 cm pot at 14 weeks of age.
Figure 2:
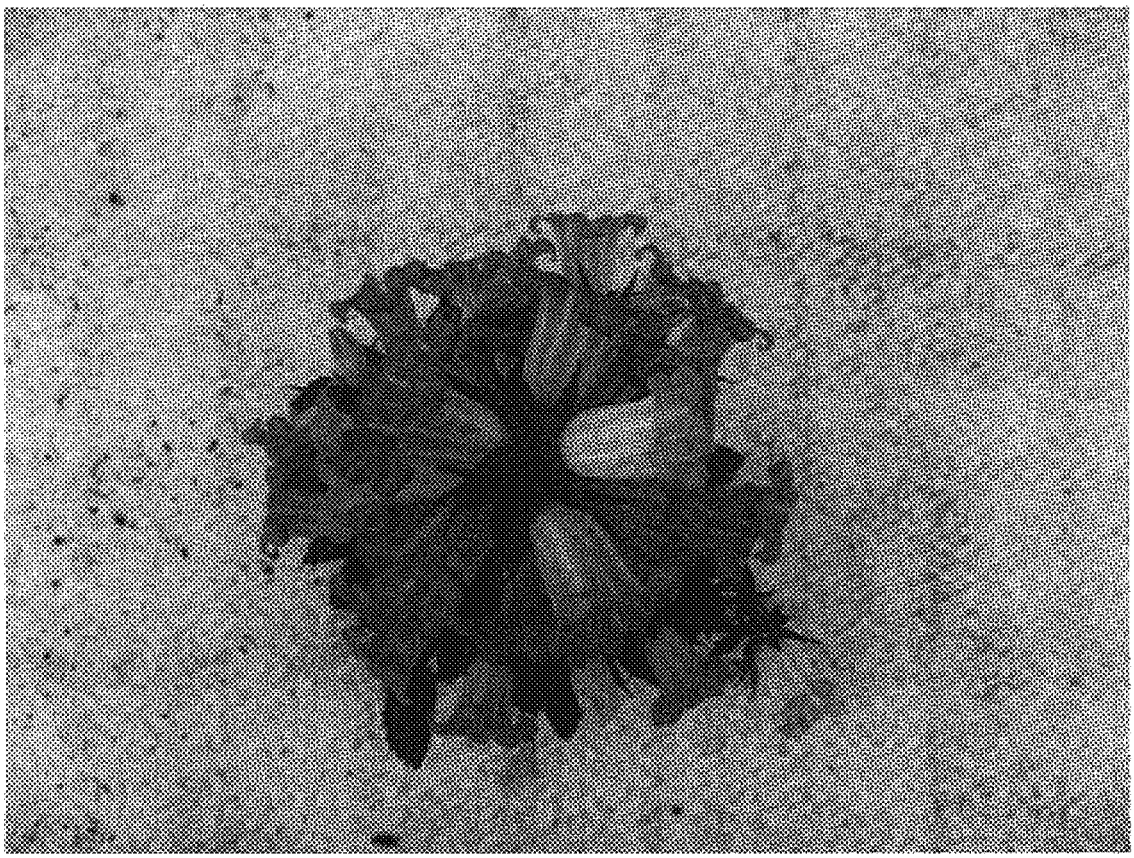
FIG. 2 shows a top perspective view of a typical flowering plant of 'PKMFOR168', as grown in a 10.5 cm pot at 14 weeks of age.
Figure 3:
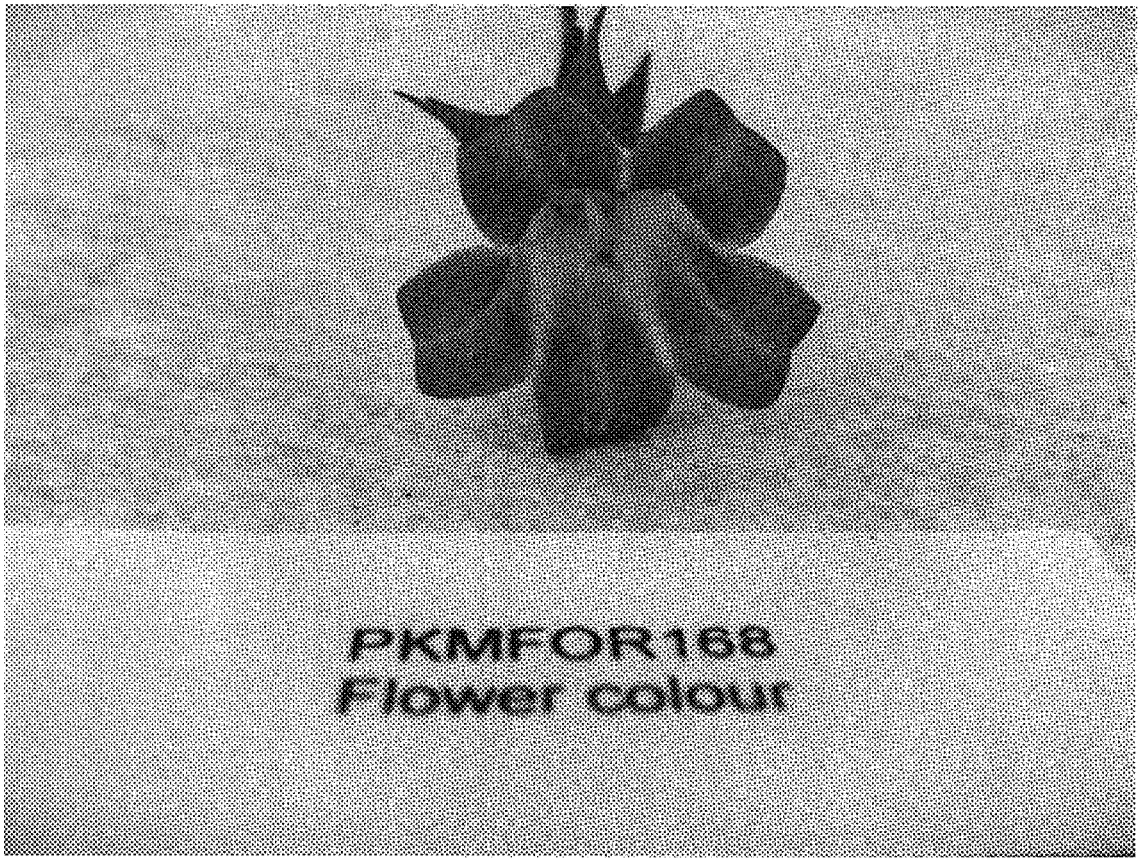
FIG. 3 show a close-up top view perspective of a typical flower produced by 'PKMFOR168' at 14 weeks of age.
Figure 4:
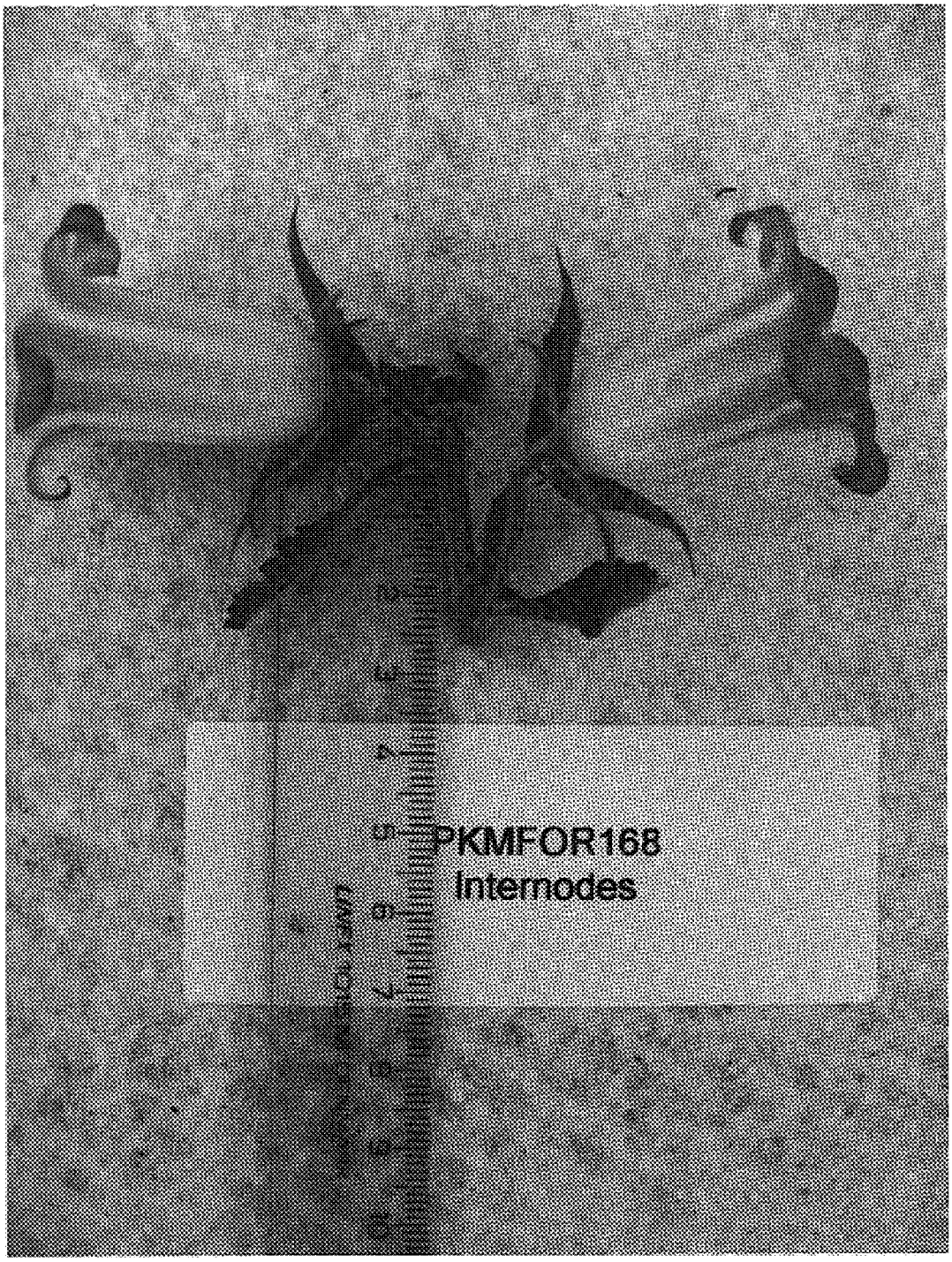
FIG. 4 show a close-up side perspective view perspective of typical flowers, including the internodes, petioles and peduncles, produced by 'PKMFOR168' at 14 weeks of age.
Figure 5:
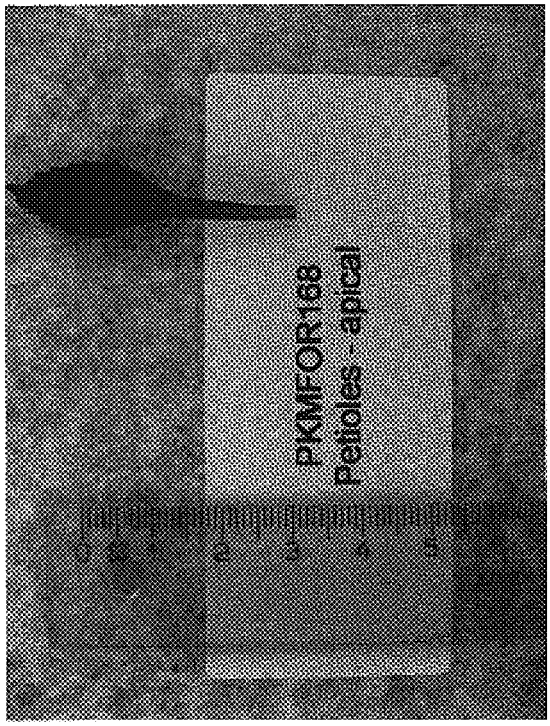
FIG. 5 show a close-up comparison view of the typical petiole of an apical leaf produced by 'PKMFOR168' at 14 weeks of age to a the typical petiole of a basal leaf produced by 'PKMFOR168' at 14 weeks of age.
Figure 5:
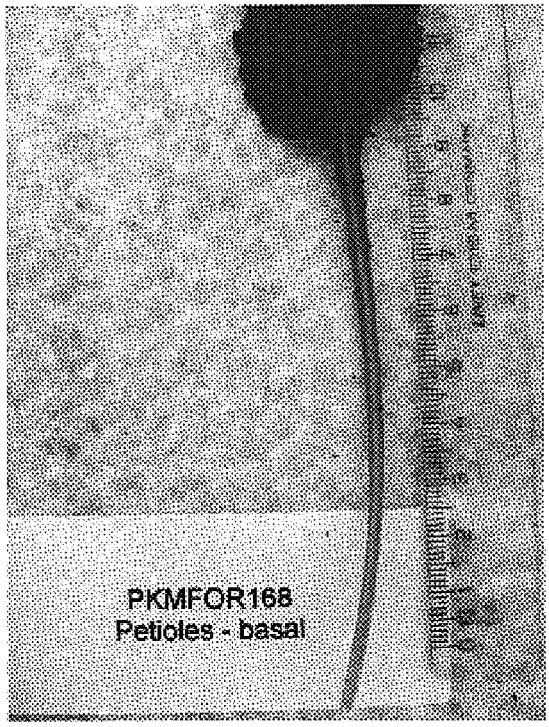

The new *Campanula* 'PKMFOR168' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMFOR168' as grown in a heated and lighted, glass-covered greenhouse in Søhus, Denmark, under conditions which closely approximate those generally used in commercial practice where day temperatures in the greenhouse range from 18–22° C. and the night temperature averages about 16° C. Ambient light levels used while growing plants of 'PKMFOR168' are +90 $Wm^2$. Plants of 'PKMFOR168' are grown with 18 hour long day photoperiodic treatments from the third week and forced to flower after cold treatment at the same day length. Propagation and seedlings are exposed to 10 hour short photoperiodic treatments. No growth retardants used.

The age of the 'PKMFOR168' plants described is 14 weeks old and grown in 10.5 cm pots. The photographs and descriptions were taken during the winter season when day temperatures in glass-covered greenhouse range from 18–20° C. and when night average temperatures in glass-covered greenhouse average 16° C.

Color references are made to The Royal Horticultural Society Colour Chart (R.H.S.), $4^{th}$ edition, except where general colors of ordinary significance are used.

Classification:

*Botanical.*—*Campanula formanekiana.*

Parentage:

*Female or seed parent.*—Unpatented cultivar from the proprietary breeding line of *Campanula formanekiana* designated 11.02.2258.

*Male or pollen parent.*—Unpatented cultivar from the proprietary breeding line of *Campanula formanekiana* designated 11.02.2253.

Propagation:

*Type cutting.*—Terminal vegetative cuttings.

*Time to initiate roots.*—About 12 to 15 days at 18 to 21° C. in tunnels in a greenhouse.

*Root description.*—Fine, well branched, fibrous.

Plant description:

*Form.*—Biennial, herbaceous plant with upright, compact plant habit. Produced as potted plant. *Campanulate* flowers in racemes. Freely branching with lateral branches forming at every node.

*Crop time.*—After rooting, about 14 to 18 weeks are required to produce finished flowering plants in 10.5 cm pots.

*Vigor.*—Vigorous growth rate.

*Plant height* (*from pot rim to top of plant plane*).—About 32 cm to 38 cm.

*Plant spread* (*width*).—About 25 cm to 30 cm.

*Lateral branches.*—Habit: Basal spreading branches and central upright stem when flowering. Quantity: About 25 to 35 per plant. Leaves per Lateral Branch: About 8 to 9. Length (including flowers): 25 cm to 35 cm. Diameter: About 2 mm to 3 mm. Internode Length: About 2 cm to 3 cm.

*Stem.*—Shape: Round. Strength: Strong. Aspect: Upright and spreading. Pubescence: Short hairs, hispidulous. Color: RHS 138B, green.

Foliage description:

*Basal leaves.*—Arrangement: Single, rosulate. Overall shape: Cordate to obovate, dentate. Apex shape: Cuspidate to rounded. Base shape: Cordate to truncate. Length: About 20 mm to 60 mm. Width: About 24 mm to 27 mm. Margin: Serate to biserate. Texture (both sides): Pubescent. Pubescence: Very short, stiff hairs on both sides, hispidulous.

*Apical* (*stem*) *leaves.*—Arrangement: Single, alternate. Overall shape: Spatulate, dentate. Apex shape: Spatulate. Base shape: Cuneate. Length: About 20 mm to 60 mm. (please confirm). Width: About 8 mm to 12 mm. Margin: Serate to biserate. Texture (both sides): Pubescent. Pubescence: Very short, stiff hairs on both sides, hispidulous.

*Basal & apical leaves.*—Foliage Color: Mature: Upper surface: Green, RHS 137A. Lower Surface: Green, RHS 138C. Immature: Upper surface: Green, RHS 137A. Lower Surface: Green, RHS 138C. Venation: Pattern: Reticulate. Color (upper and lower surface): Green, RHS 138B. Petiole: Basal Length: About 9 cm to 10 cm. Apical Length: Up to 2 cm. Diameter: 1.0 mm to 3.0 mm. Color: RHS 138B, green. Texture: Pubescent.

Inflorescence description:

*Flower arrangement and shape.*—Single, large, *campanulate* flowers in racemes turning upright to outward, basipetal flowering habit.

*Natural flowering season.*—June to July. Season can be extended by long day treatments.

*Time to flower.*—About 8 weeks after vernalization (cold treatment).

*Flower longevity.*—On the plant, flowers last about 5 to 9 days; however, longevity of individual flowers is highly dependent on temperature and light conditions. Flowers persistent.

*Fragrance.*—Slight perfume scent.

*Inflorescence size.*—Height: 15 cm to 35 cm. Diameter: 5 cm to 25 cm.

*Number of flowers per inflorescence.*—5 to 25.

*Number of flowers per lateral stem.*—5 to 10.

*Number of flowers and buds per plant.*—About 150 to 250.

*Buds.*—Length: Up to 45 mm. Diameter: Up to 12 mm. Shape: Oblong, petals forming a ribbed tube. Rate of opening: 1 to 3 per day. Color (immature): Green-white, RHS 157A. Color (mature): Base: Green-white, RHS 157C; Apex: Violet-blue, RHS 92D.

*Flowers.*—Height: About 50 to 60 mm. Diameter: About 50 mm.

*Petals.*—Arrangement: Single, sympetalous, slightly corrugated, basally fused *campanulate.* Quantity per flower: About 5. Length: Lobes about 17 mm; whole petal about 50 mm to 60 mm. Width: About 15 mm to 20 mm. Overall Shape: Sympetalous with acute lobes. Tip: Acute. Base: Fused. Margin: Entire. Texture: Silky. Color (when opening): Upper surface: Violet-blue, RHS 92B. Under surface: From violet-blue, RHS 91D at base to violet-blue, RHS 92B at lobes. Color (when fully opened): Upper surface: Violet-blue, RHS 92B, with a violet-blue, RHS 91D, distinct grove at the center and margins of each petal; Under surface: Violet-blue, RHS 92C. Fading: No fading or withering.

*Sepals.*—Arrangement: Basally fused. Appearance: Pubescent. Quantity per flower: 5. Length: About 30 mm to 40 mm. Width: About 10 to 15 mm. Overall shape: Lanceolate. Tip: Acuminate. Base: Sagittate. Margin: Serate to biserate. Texture: Pubescent, short, soft white hairs. Color (immature): Upper and under surfaces, green, RHS 138A. Color (mature): Upper and under surfaces: green, RHS 138A.

*Peduncles.*—Length: About 15 mm to 25 mm. Diameter: About 3 mm to 4 mm. Strength: Strong. Color: Green, RHS 138B.

*Pedicels.*—Angle: Acute. Length: About 40 mm to 70 mm. Diameter: About 1 mm to 2 mm. Strength: Strong. Color: Green, RHS 138B.

Reproductive organs:

*Androecium.*—Stamen: Quantity: 5, fused until pollen has shed. Anther: Shape: Lanceolate, antisepalous, introse, basifixed and two-celled. Twisting when withering. Length: About 12 mm (just before flowering opening). Color: Yellow, RHS 10C (just before flowering opening) and yellow, RHS 11B (when withering). Pollen: Amount: Plenty. Color: Yellow, RHS 10B.

*Gynoecium.*—Pistil: Quantity: 1. Length: About 30 mm to 40 mm. Stigma: Shape: Tripartite. Color: Yellow-green, RHS 149C. Style: Length: About 20–25 mm. Color: White, RHS 155A. Ovary: Color: White, RHS 155A with yellow-orange, RHS 17C, nectary.

Seed/fruit: None observed.

Weather tolerance: Plants of the new *Campanula* have exhibited good tolerance to drought, rain and wind, with low temperature resistance to 0° C.

Disease/pest resistance: Not tested.

Disease/pest susceptibility: Not tested.

I claim:

1. A new and distinct cultivar of *Campanula* plant named 'PKMFOR168', as illustrated and described herein.

* * * * *